US00PP17770P3

(12) United States Plant Patent
Whiley et al.

(10) Patent No.: US PP17,770 P3
(45) Date of Patent: May 29, 2007

(54) MANGO TREE NAMED 'B74'

(50) Latin Name: *Mangifera indica*
Varietal Denomination: B74

(75) Inventors: Anthony William Whiley, Nambour (AU); John W. Dorrian, Childers (AU)

(73) Assignee: Promised Land Avocados Pty Ltd, Childers, Queensland (AU)

( * ) Notice: Subject to any disclaimer, the term of this patent is extended or adjusted under 35 U.S.C. 154(b) by 0 days.

(21) Appl. No.: 10/811,483

(22) Filed: Mar. 26, 2004

(65) Prior Publication Data

US 2005/0216983 P1 Sep. 29, 2005

(51) Int. Cl.
*A01H 5/00* (2006.01)

(52) U.S. Cl. ..... Plt./159
(58) Field of Classification Search ..... Plt./159
See application file for complete search history.

(56) References Cited

U.S. PATENT DOCUMENTS

PP9,005 P * 12/1994 Chang ..... Plt./159

OTHER PUBLICATIONS

Bally, Ian S.E.; Species Profiles for Pacific Island Agroforestry *Mangifera indica* (mango); www.traditionaltree.org, ver. 3.1, pp. 1–24; Apr. 2006.*

Xiao et al.; Direct Somatic Embrogenesis Induced from Cotyledons of Mango Immature Zygotic Embryos; In Vitro Cell. Dev. Biol. —Plant 40: 196–199; Mar.–Apr. 2004.*

Ara et al.; Somatic Embryogenesis and Plantlet Regeneration in Amrapali and Chausa Cultivar of Mango (*Mangifera indica* L.); http://www.iisc.ernet.in/currsci/jan252000/articles4.htm; pp. 1–7.* http://www.dpi.qld.gov.au/aqldtable/12132.html.* http://www.farmindex.com.au/news.cfm?contentid=5360.* http://www.dpi.qld.gov.au/news/NewsReleases/8585.html "Dr. Tony Whiley—DPI's most prominent avocado and mango researcher retires" Feb. 15, 2002.* http://www.abc.net.au/rural/qld/stories/s479455.htm QLD Country Hour Summary Dec. 2, 2002.*

UPOV ROM GTITM Computer Database, GTI Jouve Retrival Software 2005/02 Citation for 'B74'.*

Description of 'B74' Mango (2001), Plant Varieties Journal—Official Journal of Plant Breeders Rights Australia, 14(2):45–46.

Certification of Plant Breeder's Rights (Australia) for *Mangifera indica* 'B74', granted May 20, 2002, Certificate # 1983 (one page).

Copy of Plant Breeder's Rights Application for *Mangifera indica* 'B74' (Application No. 1998/018; received Jan. 30, 1998).

* cited by examiner

*Primary Examiner*—Kent Bell
(74) *Attorney, Agent, or Firm*—Knobbe, Martens, Olson & Bear, LLP

(57) ABSTRACT

A new and distinct mango tree variety that possesses late season maturing fruits with predominately yellow and red skin, and pale yellow, firm flesh having a low amount of non-fleshy fiber attached to the stone.

7 Drawing Sheets

Latin name of the genus and species of the plant claimed: *Mangifera indica.*
Variety denomination: 'B74'.

BACKGROUND AND SUMMARY OF THE INVENTION

This invention relates to the discovery and asexual propagation of a new variety of mango tree, as herein described and illustrated. The new variety was first hybridized by controlled pollination. The new variety is a precocious, heavy-cropping, upright tree yielding red-skinned, medium-sized, terpinolene-flavored fruit.

The seed parent is 'Sensation' and the pollen parent is 'Kensington Pride.' The new variety was selected and evaluated at the fruiting stage on the property of Mr. And Mrs. L. W. Dorrian at Childers, in Queensland, Australia.

The new mango tree variety was first asexually propagated by grafting onto seedling rootstocks in Childers, in Queensland, Australia.

The new mango tree variety cv. 'B74' has been shown to maintain its distinguishing characteristics through successive asexual propagations.

BRIEF DESCRIPTION OF THE PHOTOGRAPHS

The accompanying photographic illustrations illustrate in full color the new mango variety 'B74.' The colors are as nearly true as is reasonably possible in a color representation of this type.

DETAILED BOTANICAL DESCRIPTION OF THE INVENTION

Figure 1:
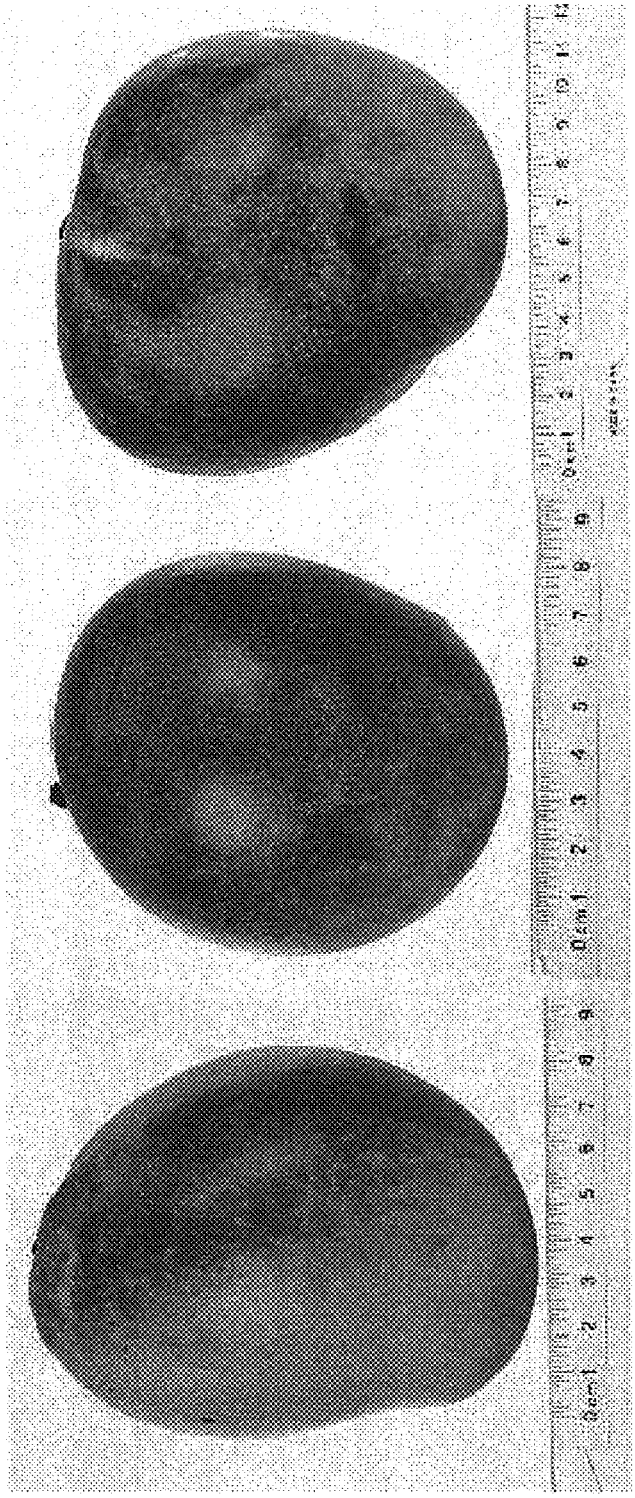
FIG. 1 is a photograph of the fruit of the new mango variety 'B74' (center) and comparators 'Kensington Pride' (bottom) and 'R2E2' (top) showing differences in size and color.
Figure 2:
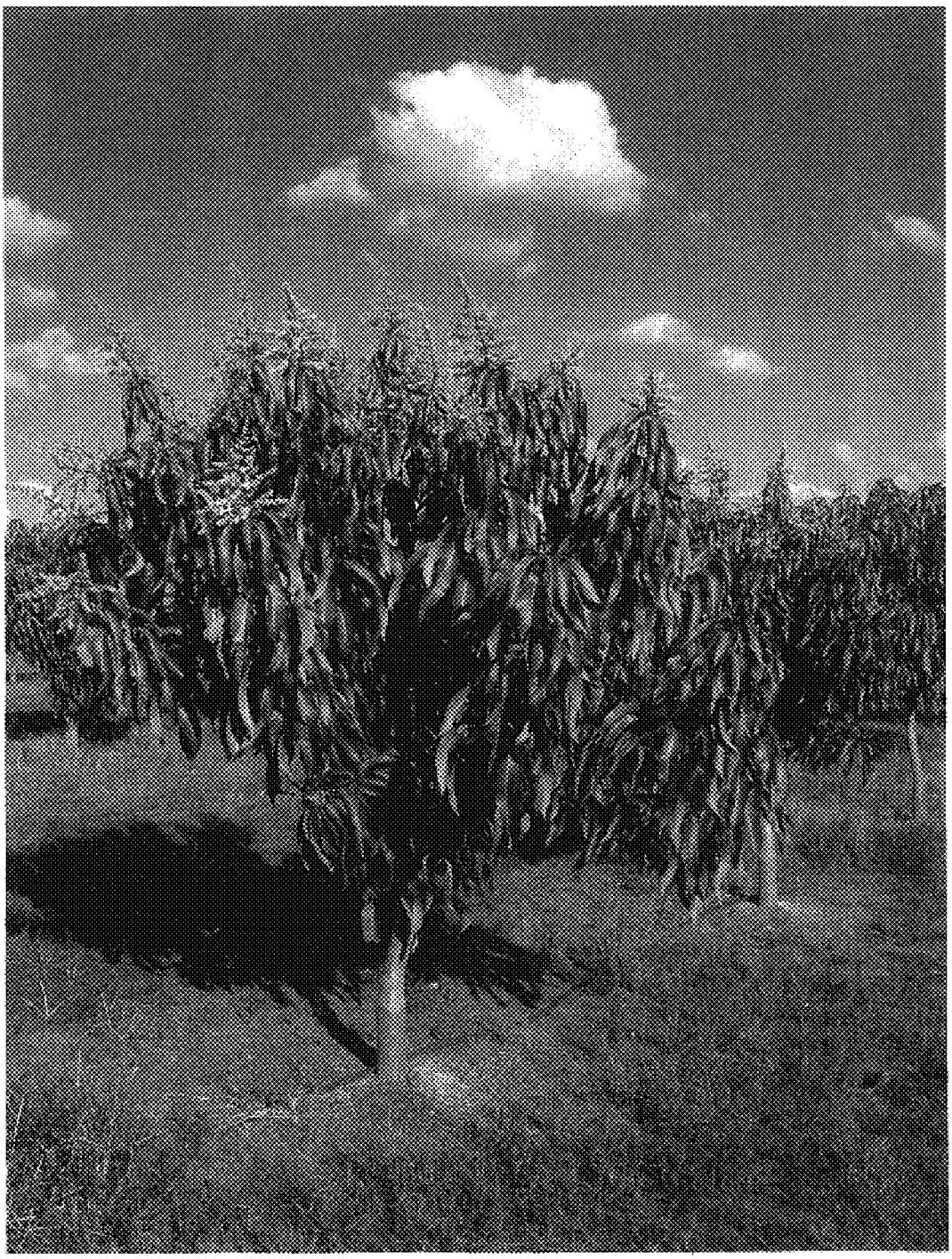
FIG. 2 is a photograph of the tree of the new mango variety 'B74.'
Figure 3:
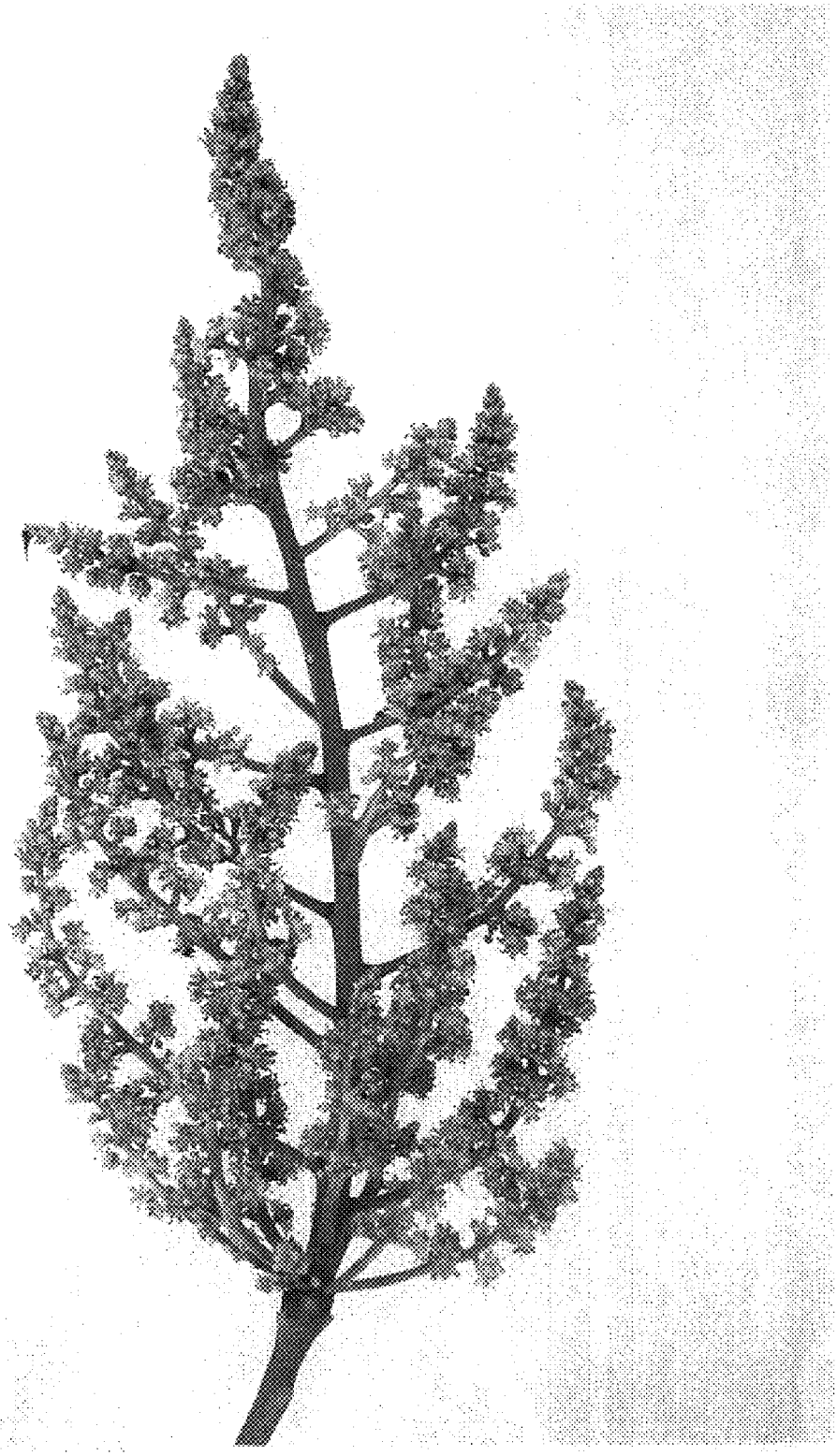
FIG. 3 is a photograph of the floral panicle of the new mango variety 'B74.'
Figure 4:
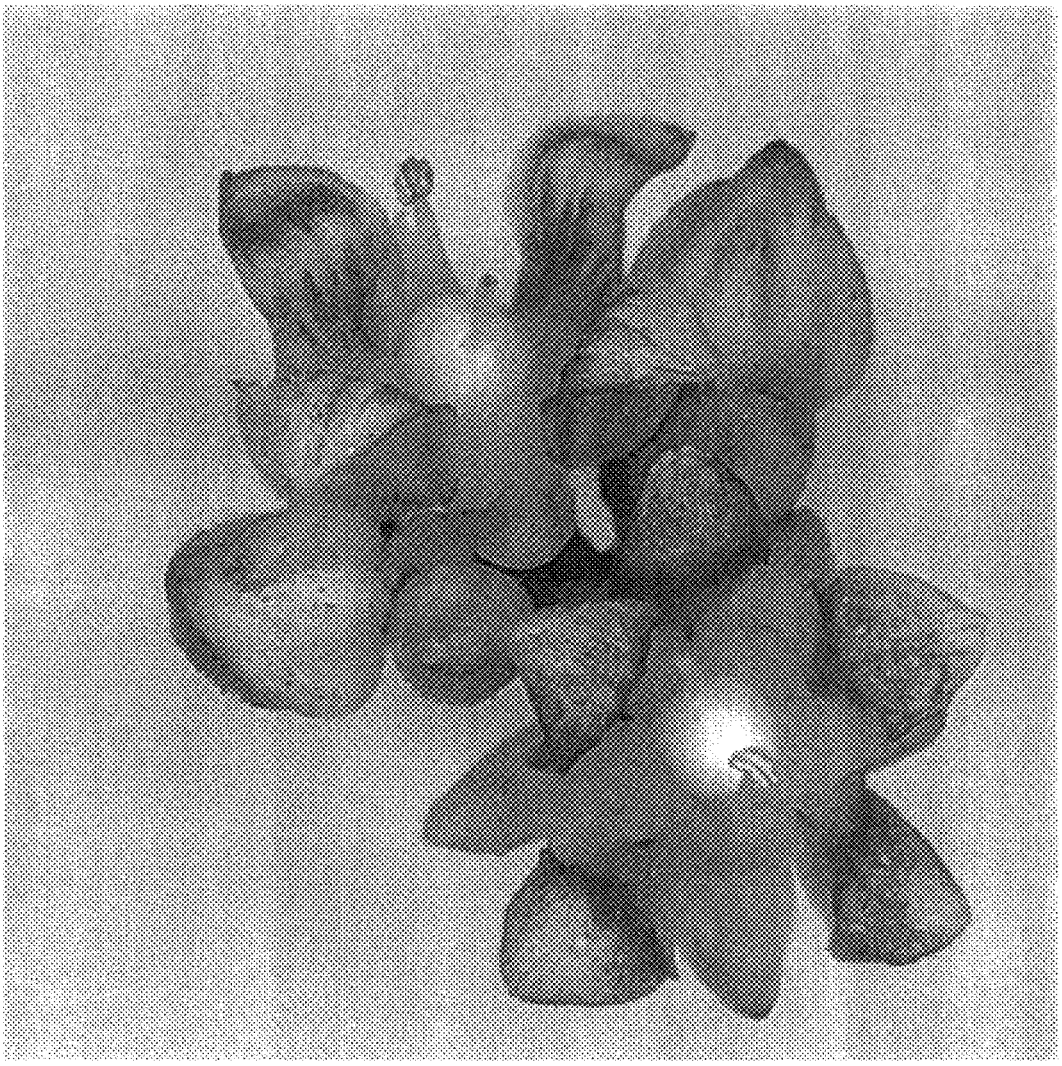
FIG. 4 is a photograph of flowers and floral buds of the new mango variety 'B74.'
Figure 5:
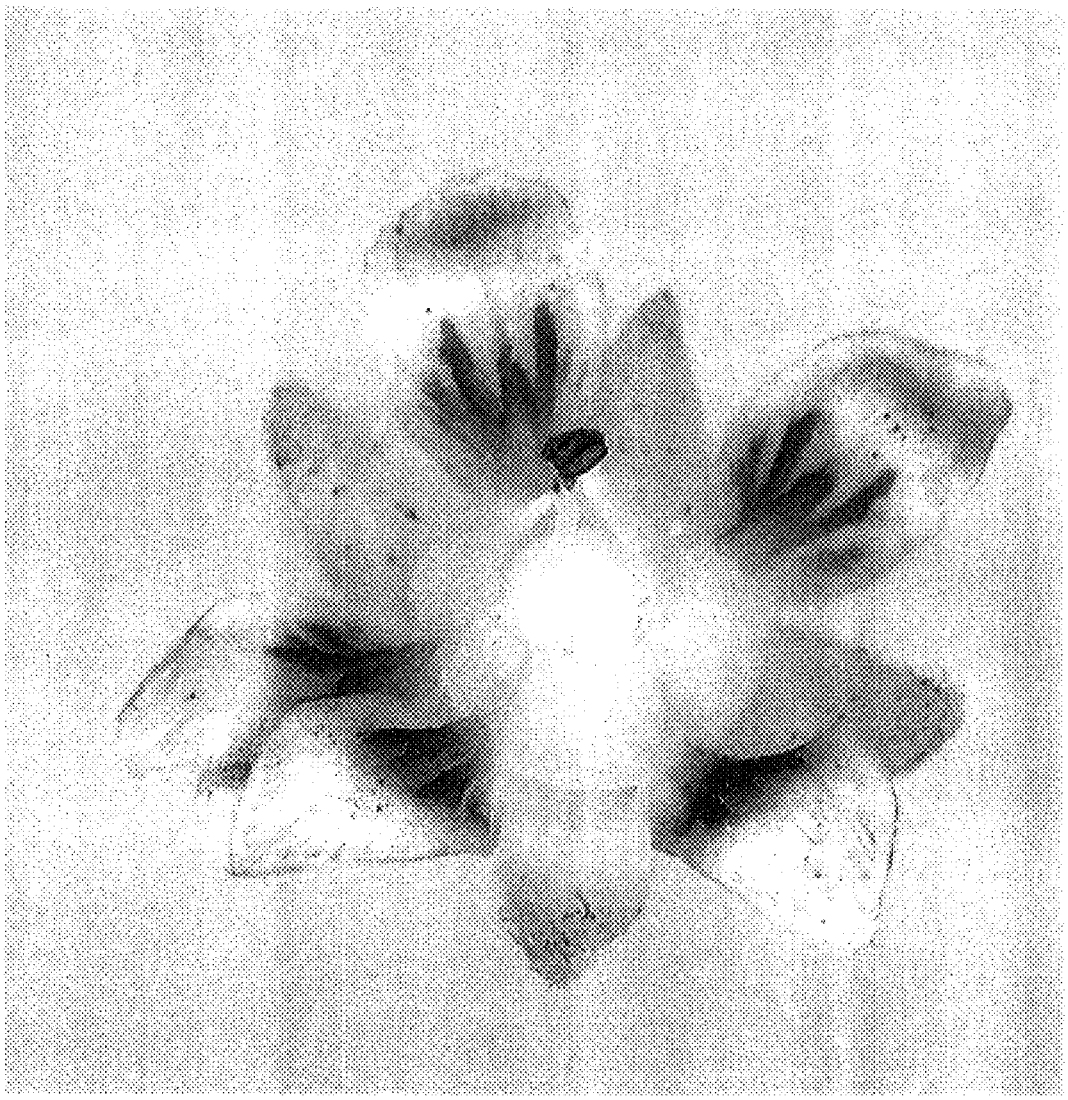
FIG. 5 is a photograph of a single flower of the new mango variety 'B74.'
Figure 6:
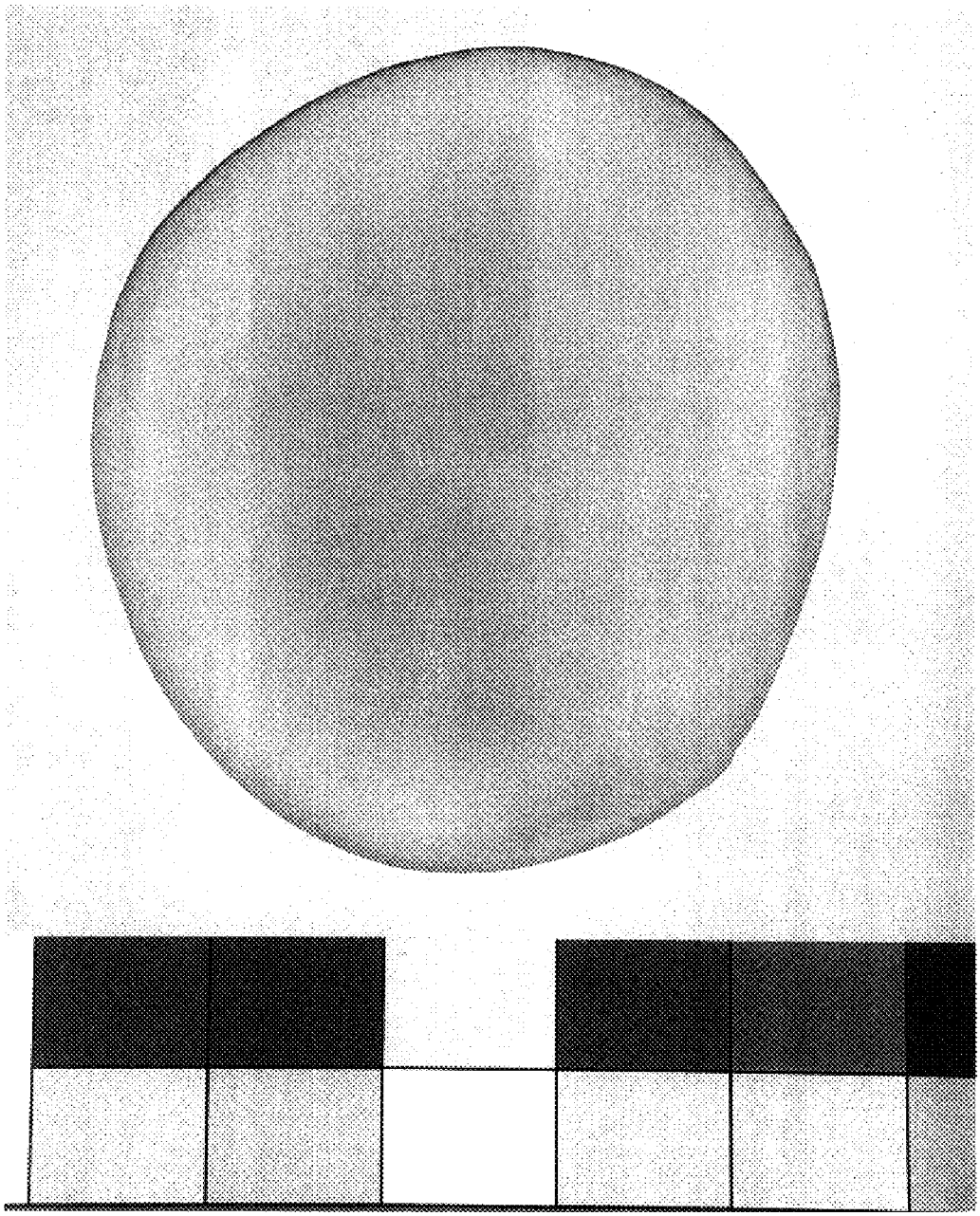
FIG. 6 is a photograph of a cross-sectional slice of the fruit of the new variety 'B74' sliced through the fruit in the region above the seed.
Figure 7:
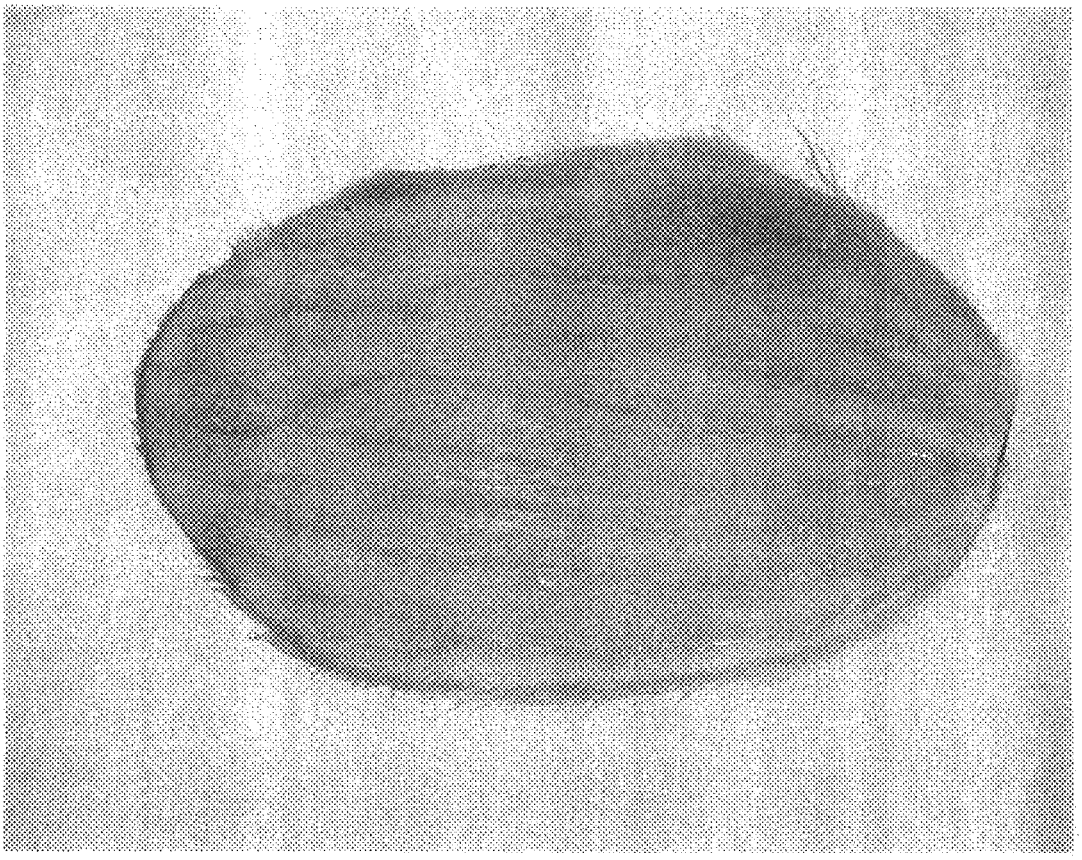
FIG. 7 is a photograph of the seed of the new mango variety 'B74.'

Throughout this specification, color names beginning with a small letter signify that the name of that color, as used in common speech, is aptly descriptive.

The descriptive matter which follows pertains to 'B74' mango trees (as well as the comparative varieties 'Sensation,' 'Kensington Pride', and 'R2E2', each of the foregoing which is unpatented) grown in the vicinity of Childers, Queensland, Australia. The scions of the candidate and comparator varieties were topworked to 'Keitt' trees (unpatented) that were originally grafted to polyembryonic seedlings of 'Kensington Pride.' Ten single tree replicates of each cultivar were planted at 6×10 m intervals in red basaltic soil (kraznozem) following a completely randomised design. Pest and disease treatments were applied as required. Irrigation and fertilizer application followed commercial practice. 10–20 random measurements of each characteristic were obtained from each replicate. Redness of skin color was determined using a Minolta Chroma Meter CR-200 to measure the hue angle (H). Mean values were taken from measurements at three points from the shoulder to the basal end of the sun-exposed side of each fruit. The lower the hue angle, the greater the red coloration. The observations described herein are believed to apply to plants of the variety grown under similar conditions of soil and climate elsewhere.

Ten single tree replicates of each cultivar were planted at 6×10 m intervals following a completely randomised design. The trees were grown on a red basaltic clay loam (kraznozem) near Childers in south east Queensland, Australia (latitude 25° S., altitude 40 m). Irrigation was available to supplement the average rainfall of 900 mm. Daily light interception (measured as photosynthetic photon flux) by tree canopies during the period of fruit development (October to February) ranges from 15.5 to 59.5 mol quanta $m^{-2}$ at this site. The mean annual maximum/minimum temperatures at this site are 24/15° C. (Australian Bureau of Meteorology).

Pest and disease treatments were applied as required. Irrigation and fertilizer application followed commercial practice. 10 to 20 random measurements of each characteristic were obtained from each replicate.

Redness of skin color was determined using a Minolta Chroma Meter CR-200 to measure the hue angle (H). Mean values were taken from measurements at three points from the shoulder to the basal end of the sun-exposed side of each fruit. The lower the hue angle, the greater the red coloration. Elsewhere throughout the specification, color references are made to The Royal Horticultural Society Color Chart. The observations described herein are believed to apply to plants of the variety grown under similar conditions of soil and climate elsewhere.

The new mango tree cultivar, 'B74' is quite distinct from its seed parent 'Sensation', and may be distinguished from its seed parent in the following characteristics: The average fruit weight of 'B74' (457 g) is larger than 'Sensation' (360 g). Additionally, the new mango tree cultivar matures 3–4 weeks earlier than the seed parent 'Sensation', which is a very late variety. The skin color of the new mango tree cultivar is red and yellow, while the skin color of the seed parent 'Sensation' has a bright yellow background with a dark red to purple blush that covers most of the surface. Further, while the new mango tree cultivar has a terpinolene aroma in both the leaves and fruit, the seed parent 'Sensation' has no distinguishable terpinolene aroma in either leaves or fruit.

The new mango tree cultivar may be distinguished from the pollen parent, 'Kensington Pride,' by the following characteristics. The tree of the new mango cultivar 'B74' has a more erect form and lower vigor than the tree of the pollen parent 'Kensington Pride'. The fruit of the new mango tree cultivar matures in late season, while the fruit of 'Kensington Pride' matures early to mid-season. The predominant skin color of ripe fruit of the new mango tree cultivar is approximately equal amounts of yellow and red blush (approximately 30% to 55% red blush), while the predominant skin color of ripe fruit of 'Kensington Pride' is yellow with a small proportion of red blush. The fruit flesh of the new mango tree cultivar is pale yellow in color, while the fruit flesh of 'Kensington Pride' is yellow. The fruit shape of the new mango tree cultivar is broad elliptic, while fruit shape of the pollen parent 'Kensington Pride' is medium elliptic. The sinus proximal of the stylar scar of the new mango tree cultivar is absent, while it is present in the pollen parent 'Kensington Pride.' The fruit of the new mango tree cultivar is somewhat smaller than that of 'Kensington Pride' (457 g as compared to 475 g). The seed of the new mango tree cultivar is of the monoembryonic type, while the seed of the pollen parent 'Kensington Pride' is polyembryonic.

The new mango tree variety 'B74' may be distinguished from presently available cultivars. The new mango tree cultivar 'B74' can be compared, for example, to 'R2E2', which is commonly grown in Australia, by the following distinguishing characteristics: The leaves of the new mango tree variety are shorter and wider than the leaves of 'R2E2.' The new mango tree cultivar has a higher percentage of bunch bearing inflorescences than 'R2E2.' The fruit of 'B74' is smaller than that of 'R2E2.' The flesh color of the new mango tree variety is pale yellow, while the flesh color of 'R2E2' is yellow. The skin color of ripe fruit of the new mango tree variety is approximately equal amounts of yellow and red blush (approximately 30% to 55% red blush), while the predominant skin color of ripe fruit of 'R2E2' is predominantly yellow with a small proportion of red blush. Additional comparative information can be found in Table 1.

TREE

General:

*Vigor.*—Low to moderate. Fruiting B74 mango trees growing at the experimental site typically produce only one flush of shoot growth annually following the completion of fruit harvest in early February. Autumn/winter temperatures typically restrict further vegetative growth prior to flowering in September—October. The mean length of summer shoot growth is approximately 26.5±2.4 mm (± values are the standard error of the mean).

*Height and spread of tree.*—At the time the description was made for Plant Breeders Rights in Australia the trees were 3 m high with a spread of 3.5 m. However, these trees were top-worked to existing 6-year-old trees. More typically nursery-produced 'B74' trees grafted to 'Kensington Pride' seedling rootstock reach approximately 1.25 m diameter and approximately 1.5 m in height by their third flowering anniversary after planting which is their first year of commercial cropping at Childers in SE Queensland.

*Density of foliage.*—Open.
*Shape.*—Upright.
*Form.*—Erect.
*Fruit bearing.*—Mid-late season maturity. Fruit maturity of 'B74' is generally reached after the accumulation of 1650 degree days (measured by the number of °C. hours accumulated above 10° C. starting from the point of full inflorescence extension). At the site where the description for 'B74' was developed, fruit reached the mature green stage during the first week of February (midseason).
*Root stock.*—'Kensington Pride'.

Trunk: The top-worked trees used for the original description for Plant Breeders Rights in Australia did not have 'B74' trunks, as they were top-worked onto 'Keitt' trees as described above. However, the trunk data supplied below have been collected from another block of 10-year-old 'B74' trees in the same orchard where 'B74' was grafted directly to seedling 'Kensington Pride' rootstocks. The position where the diameter was measured is above the graft union.
*Mean diameter of trees measured 50 cms above ground level.*—Approximately 19.3±0.3 cm.
*Trunk color.*—About Grey-brown 199A.
*Bark texture.*—Slightly rough with slight vertical ridges 10 to 20 mm apart.

BRANCHES

The branch values listed below were measured on fully mature 10-year-old 'B74' trees grafted to 'Kensington Pride' seedling rootstock.
*Branch diameter at the base.*—Approximately 10.08±0.24 cm.
*Crotch angle.*—Varies from 45 to 80°.
*Branch color.*—About Grey-brown 199A.
*Lenticels.*—Not visible.
*Surface texture.*—Slightly rough with slight vertical ridges 10 to 20 mm apart.

LEAVES

Young leaf:
*Anthocyanin.*—Present.
*Anthocyanin location on leaves.*—Leaf lamina.
*Anthocyanin coloration.*—About Greyed-orange 164A.
*Intensity of color.*—Strong.

Fully expanded leaf:
*Average length.*—Approximately 204 mm.
*Average width.*—Approximately 62 mm.
*Length/width ratio.*—Low (approximately 3.5).
*Attitude.*—Horizontal.
*Leaf surface.*—Smooth.
*Profile.*—Concave cross section.
*Shape.*—Elliptic.
*Cross-section shape.*—Concave.
*Leaf blade tip.*—Acuminate.
*Base.*—Acute.
*Symmetry.*—Asymmetric.
*Undulation of margin.*—Not undulated.
*Curvature of midrib.*—Present.
*Position of midrib curvature.*—Apical.
*Twisting of blade.*—Absent.
*Aroma present when crushed.*—Terpinolene aroma.
*Relief of upper surface of leaf.*—Slightly sunken between veins.
*Length of petiole.*—Approximately 40 mm.
*Leaf color.*—Upper surface: about Green 137A. Lower surface: about Green 138A.
*Leaf vein color.*—About Greyed-yellow 160B.
*Leaf vein pattern.*—Major veins approximately 14.04±0.64 mm apart and at approximately 80° to the midrib.
*Leaf margin shape.*—Entire.
*Stipules.*—Absent.

Petioles:
*Diameter at point of attachment.*—Approximately 3.70±0.13 mm.
*Diameter at leaf blade end.*—2.72±0.07 mm.
*Color at point of attachment.*—About Yellow-green 148B.
*Color at leaf blade end.*—About Green 138A.
*Glands.*—Absent.

INFLORESCENCE

General:
*Bearing.*—Typically bunch bearing rather than solo bearing.
*Percentage of bunch bearing inflorescences.*—Approximately 66%.
*Number of fruit per inflorescence.*—Childers growing site: approximately 3.2 through to maturity. Monsoonal tropics of northern Australia alternate site: approximately 2.4. All of the inflorescence values below have been derived from a population of 10-year-old 'B74' trees which are considered mature for this variety at Childers.
*Inflorescence length.*—Approximately 319.7±9.6 mm.
*Inflorescence diameter at the widest point.*—Approximately 175.8±5.3 mm.
*Inflorescence rachis color.*—About Red 47C.
*Inflorescence texture.*—The rachis of the inflorescence moderate pubescence.
*Mean number of inflorescences per tree.*—Approximately 316.8±27.2.
*Mean number of flowers per inflorescence.*—Approximately 764.0±32.7.
*Date of first and full blooms.*—Variable. Flowering dates vary between years and are typically influenced by the size of the preceding crop, the time that floral induction temperatures occur in the autumn/early winter and the temperatures received during the latter part of winter. Typically at the Childers site inflorescence bud break occurs in mid to late July but full bloom does not occur until the second to third week in September. To calculate Heat Accumulation Units to determine fruit maturity the time of full bloom in September is used.

FLOWERS

General:
*Diameter of open flowers.*—Approximately 7.69±0.37 mm.
*Percent hermaphrodite flowers per inflorescence.*—Approximately 34.4±6.0.
*Percent male flowers per inflorescence.*—Approximately 65.6±6.0.
*Floral fertility.*—The flowers of 'B74' are self fertile and do not require cross pollination for fruit set.

Petals:
*Number of petals per flower.*—5.
*Petal size.*—Length: approximately 3.26±0.09 mm. Diameter: approximately 2.57±0.02 mm.

*Petal texture.*—Slightly pubescent.
*Petal shape.*—Ovate.
*Petal color.*—Upper surface: about Yellow-white 158D. Lower surface: about Yellow-white 158C.

Sepals:
*Number of sepals per flower.*—5.
*Sepal size.*—Length: approximately 3.78±0.09 mm. Diameter: approximately 2.94±0.04 mm. Sepal texture: densely pubescent. Sepal shape: ovate.

Stamens:
*Stamen number in hermaphrodite flowers.*—5; typically only 2 are fertile.
*Filament length.*—Approximately 11.93±0.06 mm.
*Filament color.*—About Green-white 157D.
*Anther length.*—Approximately 0.86±0.06 mm.
*Anther shape.*—Ovate.
*Anther color.*—About Yellow-white 158B.
*Pollen color.*—About Yellow-white 158C.
*Pollen production.*—Moderately prolific; pollen viability; approximately 72.6±1.5%.

Pistils:
*Pistil number.*—1.
*Pistil shape.*—Slightly curved.
*Pistil length.*—Approximately 0.94±0.16 mm.
*Ovary number.*—1.
*Diameter of ovary.*—Approximately 1.36±0.05 mm.
*Ovary color.*—About Yellow-white 158B.

FRUIT

General harvest characteristics:
*General fruiting characteristics.*—Bunch bearing with 2–4 fruits commonly carried on each inflorescence.
*Bearing.*—When well-managed, 'B74' is a regular cropping variety producing consistent yields each year.
*Season maturity.*—Mid-late season maturity.
*Fruit yield.*—Field planted nursery-grown trees begin commercial fruiting following their 3rd flowering anniversary in the ground. For example, a nursery-grown 'B74' tree planted at Childers in the spring of 2001 will pass its first flowering anniversary in July/August 2002. The third flowering anniversary is July/August 2004 when it will set its first commercial crop. Yields recorded for the first three cropping years in a trees life are:
*Year 1.*—11.5±1.13 kg/tree.
*Year 2.*—28.84±1.93 kg/tree.
*Year 3.*—37.83±1.11 kg/tree. At Childers orchard, spacing is 8×3 m (412 trees/ha). The original small orchard planted in 1993 has a fully mature canopy producing 27 t/ha in its 10th cropping year.

Shipping and keeping characteristics of fruit:
*Shipping and keeping quality of fruit.*—'B74' mango fruit typically reached the eating ripe stage within 9–10 days of harvest under the following ripening conditions: 10 ppm ethylene for two days at 20° C. followed by holding at 20° C. (no ethylene) until eating ripe stage. Once fruit reaches the eating ripe stage, it remains firm and in an acceptable saleable condition for a further 9–10 days when held at 20° C.
*Long term storage.*—Long term storage assessments have not been completed on this variety but early indications are that it will hold in a firm condition for 18–21 days at 12° C. and then ripen to an acceptacle saleable condition.
*Bruising.*—Bruising of mature green 'B74' fruit in transit has not been of commercial significance, with fruit traveling up to 3000 km by road transport.

MATURE FRUIT

General:
*Length.*—Medium — approximately 101.3 mm.
*Width.*—Medium — approximately 91.3 mm.
*Length/width ratio.*—Medium — approximately 1.1.
*Shape.*—Ovate.
*Cross-sectional shape.*—Broad elliptic.
*Average weight.*—Approximately 457 g.
*Stalk cavity.*—Shallow.
*Sinus proximal of stylar scar.*—Absent.
*Bulge proximal of stylar scar.*—Absent.

Skin of mature fruit:
*Ground color.*—About Yellow-orange 20A.
*Anthocyanin coloration (blush).*—Skin develops high levels of red anthocyanin pigmentation (about Red 4A) where exposed to sun.
*Percentage of blush covering of fruit.*—Approximately 30–55%.
*Skin thickness.*—Thin; about 1.3 mm.
*Adherence of flesh to skin.*—Moderate.
*Lenticel spotting.*—Occurs over the surface of the skin and is more prominent on the blush areas.
*Lenticel spot color.*—About Green-yellow 1C.
*Lenticel size.*—Less than approximately 0.4 mm in diameter.

RIPE FRUIT

Skin of ripe fruit:
*Redness of skin color (hue angle).*—Approximately 44.7 (using a Minolta Chroma Meter CR-200).

Flesh of ripe fruit:
*Main color of flesh.*—About Yellow-orange 15A.
*Firmness of flesh.*—Firm. The firmness of ripe fruit determined by penetrometer is approximately 2.0±0.29 Kg.
*Flavor characteristics.*—Approximately 14.73±1.44 °Brix and 0.183±0.072% acidity.
*Texture of flesh.*—Smooth.
*Amount of non-fleshy fiber in flesh attached to stone.*—Low.
*Turpinolene flavor.*—Present.
*Sap exudation at harvest.*—Present with sap burn and skin browning.

SEED AND ENDOCARP

Endocarp surface: Moderately fibred with the flesh adhering to its surface.

Endocarp surface color: About Yellow-orange 17B due to the adhering flesh.

Endocarp plus seed dimensions:
*Mean weight.*—Approximately 30.92±1.42 g.
*Mean length.*—Approximately 67.67±0.23 mm.
*Longest diameter.*—Approximately 40.10±0.89 mm.

Monoembryonic seed removed from the endocarp:
*Mean weight.*—Approximately 15.27±0.66 g.
*Mean length.*—Approximately 57.26±1.15 mm.
*Longest diameter.*—Approximately 31.38±0.94 mm.

Seed color: About Yellow-white 158D. Seed size: small.

Polyembryony: Monoembryonic.

The numerical data presented in the Australian Plant Breeders Rights description of 'B74' (see Table 1, below) have been derived from trees planted in a replicated, randomised block design with the mean values derived from an Analysis of Variance (Genstat 8.1). LSD=Least Significant Difference and is the value determined to differentiate statistical differences between the candidate variety and its comparators. Sig=the level at which statistical difference has been determined, i.e. P<0.01 indicates a 99% confidence level in the result obtained. "ns"=not significant and indicates that there is no statistical difference in this parameter between the candidate variety and the comparator.

TABLE I

COMPARISON OF 'B74' WITH OTHER MANGO VARIETIES

| | 'B74' | 'Kensington Pride' | 'R2E2' |
|---|---|---|---|
| | YOUNG LEAF | | |
| Anthocyanin | present | present | present |
| Anthocyanin hue | red | red | red |
| Intensity of color | strong | strong | strong |
| | MATURE LEAF | | |
| Terpinolene aroma | present | present | absent |
| Cross-section shape | concave | concave | straight |
| Relief of upper surface | slightly sunken between veins | raised between veins | raised between veins |
| Shape of tip | acuminate | attenuate | acuminate |
| Shape of base | acute | acute | rounded |
| Predominant shape | elliptic | elliptic | elliptic |
| Symmetry | asymmetric | asymmetric | asymmetric |
| Curvature of midrib | present | present | present |
| Attitude | horizontal | horizontal | horizontal |
| Petiole length (mm) | | | |
| Mean | 39.8 | 21.3 | 35.5 |
| std deviation | 0.7 | 0.7 | 1.0 |
| LSD/sig | 0.6 | P ≦ 0.01 | P ≦ 0.01 |
| Lamina length (mm) | | | |
| Mean | 203.9 | 181.5 | 236.8 |
| std deviation | 3.9 | 6.2 | 4.4 |
| LSD/sig | 2.0 | P ≦ 0.01 | P ≦ 0.01 |
| Lamina width (mm) | | | |
| Mean | 62.3 | 39.7 | 51.8 |
| std deviation | 0.8 | 1.1 | 0.8 |
| LSD/sig | 1.30 | P ≦ 0.01 | P ≦ 0.01 |
| Length/width ratio | | | |
| Mean | 3.44 | 4.00 | 4.00 |
| std deviation | 0.89 | 1.11 | 0.96 |
| LSD/sig | 0.21 | P ≦ 0.01 | P ≦ 0.01 |
| | INFLORESCENCE | | |
| Percentage of bunch-bearing inflorescences | | | |
| Mean | 66.4 | 22.9 | 34.3 |
| std deviation | 9.0 | 9.1 | 10.1 |
| LSD/sig | 11.7 | P ≦ 0.01 | P ≦ 0.01 |
| | MATURE FRUIT | | |
| Cross-sectional shape | broad elliptic | medium elliptic | broad elliptic |
| Depth of stalk cavity | shallow | medium | medium |
| Sinus proximal of stylar scar | absent | present | absent |
| Bulge proximal of stylar scar | absent | absent | absent |
| Ripe fruit: predominant skin color | approximately equal amounts of yellow and red blush | predominantly yellow with a small proportion of red blush | predominantly yellow with a small proportion of red blush |

TABLE I-continued

COMPARISON OF 'B74' WITH OTHER MANGO VARIETIES

| | 'B74' | 'Kensington Pride' | 'R2E2' |
|---|---|---|---|
| Ripe fruit: predominant flesh color | pale yellow | yellow | yellow |
| Ripe fruit: amount of fiber in flesh attached to stone | low | medium | low |
| Ripe fruit: terpinolene flavor | present | present | absent |
| Length (mm) | | | |
| Mean | 101.23 | 113.52 | 117.11 |
| std deviation | 2.68 | 2.14 | 3.34 |
| LSD/sig | 3.43 | P ≦ 0.01 | P ≦ 0.01 |
| Width (mm) | | | |
| Mean | 91.28 | 87.94 | 111.98 |
| std deviation | 2.80 | 2.71 | 2.43 |
| LSD/sig | 3.17 | P ≦ 0.01 | P ≦ 0.01 |
| Length/Width ratio | | | |
| mean | 1.11 | 1.29 | 1.05 |
| std deviation | 0.01 | 0.03 | 0.01 |
| LSD/sig | 0.02 | P ≦ 0.01 | P ≦ 0.01 |
| Weight (g) | | | |
| mean | 457.4 | 475.1 | 802.7 |
| std deviation | 38.1 | 37.0 | 53.0 |
| LSD/sig | 50.5 | ns | P ≦ 0.01 |
| *Ripe color (hue angle) | | | |
| mean | 44.73 | 67.36 | 53.50 |
| std deviation | 4.18 | 2.05 | 2.58 |
| LSD/sig | 3.41 | P ≦ 0.01 | P ≦ 0.01 |
| Embryonic type | mono-embryonic | Polyembryonic | mostly polyembryonic |
| | TREE | | |
| Form | erect | Spreading | erect |
| Vigor | low-moderate | high | moderate |
| Fruit maturity season | late | Early-mid | mid-late |

*Redness of skin color was determined using a Minolta Chroma Meter CR-200 to measure the hue angle (H).

TABLE 2

COMPARISON OF 'B74' FRUIT COLOR WITH OTHER MANGO VARIETIES

| Variety | Skin color: Ground color | Skin color: Blush color | Flesh color |
|---|---|---|---|
| B74 | 20A (yellow-orange) | 4A (red) | 15A (yellow-orange) |
| Kensington Pride | 20A (yellow-orange) | 26B (orange) | 21B (yellow-orange) |
| R2E2 | 22A (yellow-orange) | 179A (greyed-red) | 23A (yellow-orange) |

What is claimed is:

1. A new and distinct mango tree named 'B74' as herein described and illustrated.

* * * * *